(12) United States Patent
Franklin et al.

(10) Patent No.: US 6,738,657 B1
(45) Date of Patent: May 18, 2004

(54) CUSTOMIZED SURGICAL FIXTURE

(75) Inventors: Ronald J. Franklin, Bowdoinham, ME (US); Joel I. Franck, Durham, ME (US); Frederick C. Haer, Brunswick, ME (US)

(73) Assignee: Neutar L.L.C., Bowdoinham, ME (US)

( * ) Notice: Subject to any disclaimer, the term of this patent is extended or adjusted under 35 U.S.C. 154(b) by 0 days.

(21) Appl. No.: 09/869,551

(22) PCT Filed: Jul. 2, 1999

(86) PCT No.: PCT/US99/15006
§ 371 (c)(1),
(2), (4) Date: Dec. 4, 2002

(87) PCT Pub. No.: WO00/01316
PCT Pub. Date: Jan. 13, 2000

Related U.S. Application Data

(63) Continuation of application No. 09/110,070, filed on Jul. 6, 1998, now Pat. No. 6,327,491.

(51) Int. Cl.$^7$ ................................................. A61B 5/05
(52) U.S. Cl. ....................................................... 600/429
(58) Field of Search ................................ 600/437, 429, 600/426, 424, 407, 411, 427, 414; 606/130, 73; 164/45

(56) References Cited

U.S. PATENT DOCUMENTS

| | | | |
|---|---|---|---|
| 4,256,112 A | | 3/1981 | Kopf et al. |
| 4,805,615 A | * | 2/1989 | Carol .......................... 606/130 |
| 5,107,839 A | | 4/1992 | Houdek et al. |
| 5,116,345 A | * | 5/1992 | Jewell et al. ................ 606/130 |
| 5,222,499 A | * | 6/1993 | Allen et al. .................. 600/426 |
| 5,263,956 A | * | 11/1993 | Nobles ......................... 606/130 |
| 5,298,115 A | | 3/1994 | Leonard |
| 5,300,076 A | * | 4/1994 | Leriche ........................ 606/73 |

(List continued on next page.)

FOREIGN PATENT DOCUMENTS

| | | |
|---|---|---|
| WO | WO 95/13758 | 5/1995 |
| WO | WO 96/11624 | 4/1996 |
| WO | WO 00/01316 | 1/2000 |

OTHER PUBLICATIONS

Stratasys, Inc., FDM2000 Rapid Prototyping System Website Brochure.

*Primary Examiner*—Francis J. Jaworski
*Assistant Examiner*—Ruby Jain
(74) *Attorney, Agent, or Firm*—Fish & Richardson P.C.

(57) ABSTRACT

A customized surgical fixture (400) is formed by scanning a body to form a three-dimensional image of the body, and then identifying in the image a target (310) in the body, and mounting points or structures (330) on the body. A model, such as a computer solid model, of the fixture (400) is specified in accordance with the locations of the target (310) and mounting structures (330) or points. The fixture (400) is formed in accordance with the model of the fixture (400), for example using a rapid prototyping and tooling machine. When attached to the body, the fixture (400) can be used to guide a surgical instrument (610) into the body, for example, by using a mechanical guide (600) attached to the fixture (400) or using a remote sensing device (1300) that tracks the relative position of the customized fixture (400) and the surgical instrument.

25 Claims, 15 Drawing Sheets

U.S. PATENT DOCUMENTS

| | | | |
|---|---|---|---|
| 5,365,996 A | * 11/1994 | Crook | 164/45 |
| 5,370,692 A | 12/1994 | Fink et al. | |
| 5,397,329 A | * 3/1995 | Allen | 606/73 |
| 5,531,229 A | 7/1996 | Dean et al. | |
| 5,595,703 A | 1/1997 | Swaelens et al. | |
| 5,627,949 A | 5/1997 | Letcher, Jr. | |
| 5,638,819 A | * 6/1997 | Manwaring et al. | 600/424 |
| 5,702,406 A | 12/1997 | Vilsmeier et al. | |
| 5,728,106 A | 3/1998 | Misko et al. | |
| 5,732,703 A | * 3/1998 | Kalfas et al. | 600/407 |
| 5,741,215 A | 4/1998 | D'Urso | |
| 5,768,134 A | 6/1998 | Swaelens et al. | |
| 5,776,143 A | * 7/1998 | Adams | 606/130 |
| 5,807,252 A | * 9/1998 | Hassfeld et al. | 600/407 |
| 5,823,778 A | 10/1998 | Schmitt et al. | |
| 5,891,157 A | * 4/1999 | Day et al. | 606/130 |
| 5,891,158 A | * 4/1999 | Manwaring et al. | 606/130 |
| 5,967,982 A | * 10/1999 | Barnett | 600/429 |
| 5,978,696 A | * 11/1999 | VomLehn et al. | 600/411 |
| 5,980,535 A | * 11/1999 | Barnett et al. | 606/130 |
| 5,987,349 A | * 11/1999 | Schulz | 600/427 |
| 6,006,126 A | * 12/1999 | Cosman | 600/426 |
| 6,011,987 A | * 1/2000 | Barnett | 600/414 |
| 6,026,315 A | * 2/2000 | Lenz et al. | 600/414 |

* cited by examiner

CUSTOMIZED SURGICAL FIXTURE

This application is a continuation of 09/110,070 filed Jul. 6, 1998 now U.S. Pat. No. 6,327,491.

BACKGROUND

The invention relates to customized surgical fixtures. Many types of surgical procedures rely on precisely guiding an instrument into the body. This is the case in stereotactic surgery in which a target point within a body, for example, within a brain, is identified in a three-dimensional scanned image of the body. A detailed survey of stereotactic surgery can be found in *Textbook of Stereotactic and Functional Neurosurgery*, P. L. Gildenberg and R. R. Tasker (eds.), McGraw-Hill, June 1997 (ISBN: 0070236046). In a typical approach to stereotactic surgery, a frame is attached to the body prior to scanning. After scanning, the target point in the body is identified in the scanned image with reference to the frame. Then, during surgery, an adjustable instrument guide is attached to the frame. The guide is adjusted to align with the target point. A related approach to stereotactic surgery is described in copending U.S. patent application Ser. 09/063,658 filed Apr. 21, 1998, which is incorporated herein by reference. In that approach applied to brain surgery, an adjustable instrument guide is attached directly to the skull. Once attached, it is adjusted to align with the target point.

These previous approaches to stereotactic surgery require adjustment of an instrument guide in order that the instrument can be driven accurately to the target point within the body.

SUMMARY

Adjusting an instrument guide to align with a target point within the body can be complex and time consuming. In some procedures multiple points must be targeted. For example, in spinal sterotactic surgery, multiple targets on different spinal segments are used. In a general aspect of the invention, rather than targeting an adjustable instrument guide, a customized fixture is fabricated for a particular patient, such that targeting is unnecessary or greatly simplified. A fixed instrument guide attached to the customized fixture can be used to guide a surgical instrument to the desired point without adjustment.

In one aspect, the invention features a method for forming a surgical fixture for attaching to a body and providing a reference structure for precisely locating a target within the body, such as a particular point or an anatomical structure within the body. The method includes processing a three-dimensional scanned image of the body, for example a CT or MRI scan. The scanned image includes the target within the body, for example a point or region of the body, and a mounting location of the body. The method also includes determining a structure of the surgical fixture such that when attached at the mounting location of the body the fixture provides a reference structure in a determined location and orientation with respect to the target within the body.

The method can include one or more of the following features.

Multiple mounting points can be identified in the scanned image. The geometric relationship between corresponding mounting points on the fixture and the reference structure can then be determined. The method can further include attaching mounting anchors to the body prior to scanning the body. Scanning markers are attached to the anchors. The identified mounting points are then the locations of the scanning markers in the three-dimensional image.

The mounting location for the fixture can be an anatomical structure on the body. A contour of a surface of the fixture is determined to mate with the anatomical structure.

The method can include identifying the target in the scanned image. Also, a trajectory for reaching the target can be identified. The location and orientation of the reference structure is then determined with respect to the identified trajectory.

The structure of the fixture can be determined in terms of a solid model of the fixture which defines the volume enclosed by the surface of the fixture. The method can then also include fabricating the fixture according to the solid model.

The method can include attaching the surgical fixture to the body and guiding an instrument to the target with reference to the attached surgical fixture.

The method can include attaching the surgical fixture to the body and attaching multiple tracking markers to the surgical fixture. For example, the multiple tracking markers, such a light-emitting diodes, can be attached to a tracking fixture that is then attached to the surgical fixture. The method then includes tracking locations of the tracking markers relative to a remote sensing device, such as a camera array or a laser tracker. The method can further include tracking a location of a surgical instrument relative to the remote sensing device, for example by tracking locations of tracking markers attached to the instrument, and computing a relative position of the surgical instrument to the surgical fixture using the tracked location of the tracking markers and the surgical instrument relative to the remote sensing device.

The method can also include attaching a second surgical fixture at a second mounting location of the body, and attaching multiple tracking markers to the second surgical fixture. For example, the two surgical fixtures are attached at two mounting points on an articulated portion of the body, for example, on two bones coupled at a skeletal joint. The method then includes tracking locations of the tracking markers attached to the second surgical fixture relative to the remote sensing device and computing a relative position of the two mounting locations of the body from the tracked locations of the tracking markers attached to both surgical fixtures. For example, a configuration of a skeletal joint can be determined from the computed relative position of the mounting locations.

The body can include a spine and the mounting location can include a spinal segment. The method can also include forming a model of the spine. The method can further include forming a corrected model of the spine in a corrected configuration. The determined structure of the surgical fixture is such that when attached, the fixture provides a second reference structure in a determined location and orientation with respect to the target in the corrected configuration of the spine.

The method can include selecting a model of a standard fixture and deforming the model of the standard fixture in order to match the standard model to the target and the mounting location.

In another aspect, the invention features a surgical fixture formed from a computer model using a rapid prototyping and tooling technique. The fixture includes multiple mounting sections for attaching the fixture to a body at a predetermined mounting location on a body and a reference structure coupled to the mounting sections for guiding a surgical instrument into the body. When the fixture is attached to the body at the mounting location the reference structure is at a predetermined location and orientation to a target within the body. The fixture can include an instrument guide mounted on the reference structure for driving the instrument into the body.

In another aspect, the invention features software stored on a computer readable medium for causing a computer to perform the functions of processing a three-dimensional scanned image of a body, the scanned image including the target within the body and a mounting location of the body and determining a structure of a surgical fixture such that when attached at the mounting location of the body the fixture provides a reference structure in a determined location and orientation with respect to a target within the body.

Advantages of the invention include avoiding the need for targeting of an adjustable guidance fixture based on the location of target points within the body. This reduces the time required for surgery, and can increase the accuracy and precision of targeting.

Another advantage is that the customized fixture can provide a mounting base in a precise location relative to the body. This avoids a manual registration procedure of stereotactic surgery in which a correspondence between the scanned image and the physical body is established. The manual registration procedure can be time consuming and inaccurate.

Another advantage is that tracking markers, such as light sources or reflectors, can be attached at predetermined locations relative to the body, without requiring that mounting points, such as bone anchors, are in a particular configuration, and without requiring a manual registration step after the tracking markers are attached to the body. This provides flexibility in the choice of where to mount the fixture and reduces the time required before surgery can begin and provides improved accuracy compared to that typically achieved using manual registration and avoids errors inherent in a manual registration step.

Another advantage is that the customized fixture is easily attached to the body, for instance by mating the fixture to a set of anchors attached to the body prior to scanning, or in another instance, mating the fixture to the particular anatomy of the patient.

Another advantage is that the customized fixture can be repeatedly reattached to permanently implanted anchors in the body allowing follow-up or repeated procedures.

Another advantage of the invention is that the detailed fixture design can be based on a desired configuration of a configurable portion of the body, such as the spine, rather than solely on the configuration during scanning. This allows the fixture to be used not only to guide instruments into the body, but when attached to the body, to constrain the configuration of the body, such as correcting a spinal or orthopedic bone deformity or complex fracture.

Other features and advantages of the invention will be apparent from the following description, and from the claims.

DESCRIPTION

An approach to stereotactic surgery according to the invention involves four phases.

Scanning and Surgical Planning. A three-dimensional scanned image of a patient is taken. A surgeon identifies a target point or volume within the body and determines coordinates of the target in the image.

Fixture Design. Based on the scanned image and the identified target point, a computer "solid model" of a customized fixture is computed. The solid model is computed so that the resulting fixture can be precisely attached to the body. The fixture is further designed to include an integral instrument guide, or a mounting base for a removable guide, for accurately positioning a surgical instrument at the target point when the fixture is attached to the body.

Fixture Fabrication. Based on the computed solid model, the customized fixture is fabricated using a computer controlled rapid prototyping and tooling (RPT) technique.

Surgery. The fabricated customized fixture is attached to the patient, and a surgical instrument is guided to the target point using the fixture.

Brain Surgery

A first embodiment of the invention is directed to brain surgery. Several alternative embodiments, described below, are also directed to brain surgery. Additional related embodiments are also applicable to other types of surgery, including spinal surgery. The first embodiment, which is directed to brain surgery, is described below following the four phases summarized above.

Scanning and Surgical Planning Phase

Figure 1A:
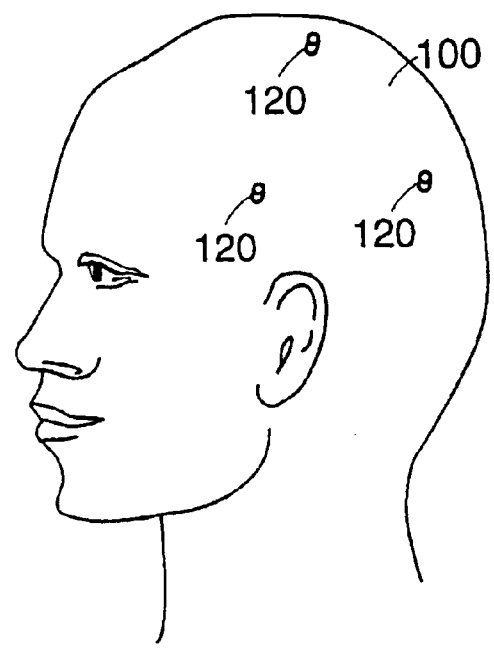
FIGS. 1a–b show scanning markers and bone anchors used to attached the scanning markers to a skull.

Referring to FIG. 1a, in the first phase, the scanning and surgical planning phase, a set of bone anchors 120 is attached to the skull 100 prior to scanning the patient. In the illustrative example shown in FIG. 1, three bone anchors 120 are attached to the skull. A greater or smaller number of anchors can also be used. During the later surgical phase, bone anchors 120 will be the attachment points for the fabricated fixture.

Figure 1B:
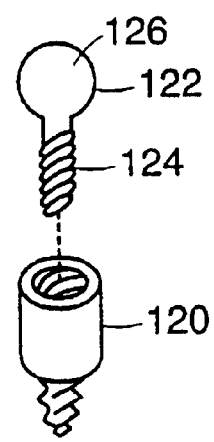

Referring to FIG. 1b, each of the bone anchors 120 has a threaded opening for accepting threaded bolts or other threaded attachments. In particular, prior to scanning, each threaded opening is used to accept a scanning marker 122. Each scanning marker 122 includes a threaded section 124 attached to a marker portion 126.

Marker portion 126 includes a material that will result in a visible image in the scanned image. Various types of scanning techniques can be used, including CT, PET, MRI, SPECT, and laser. The material in the marker portions 126 is chosen depending on the scanning technique that will be used.

Figure 2:
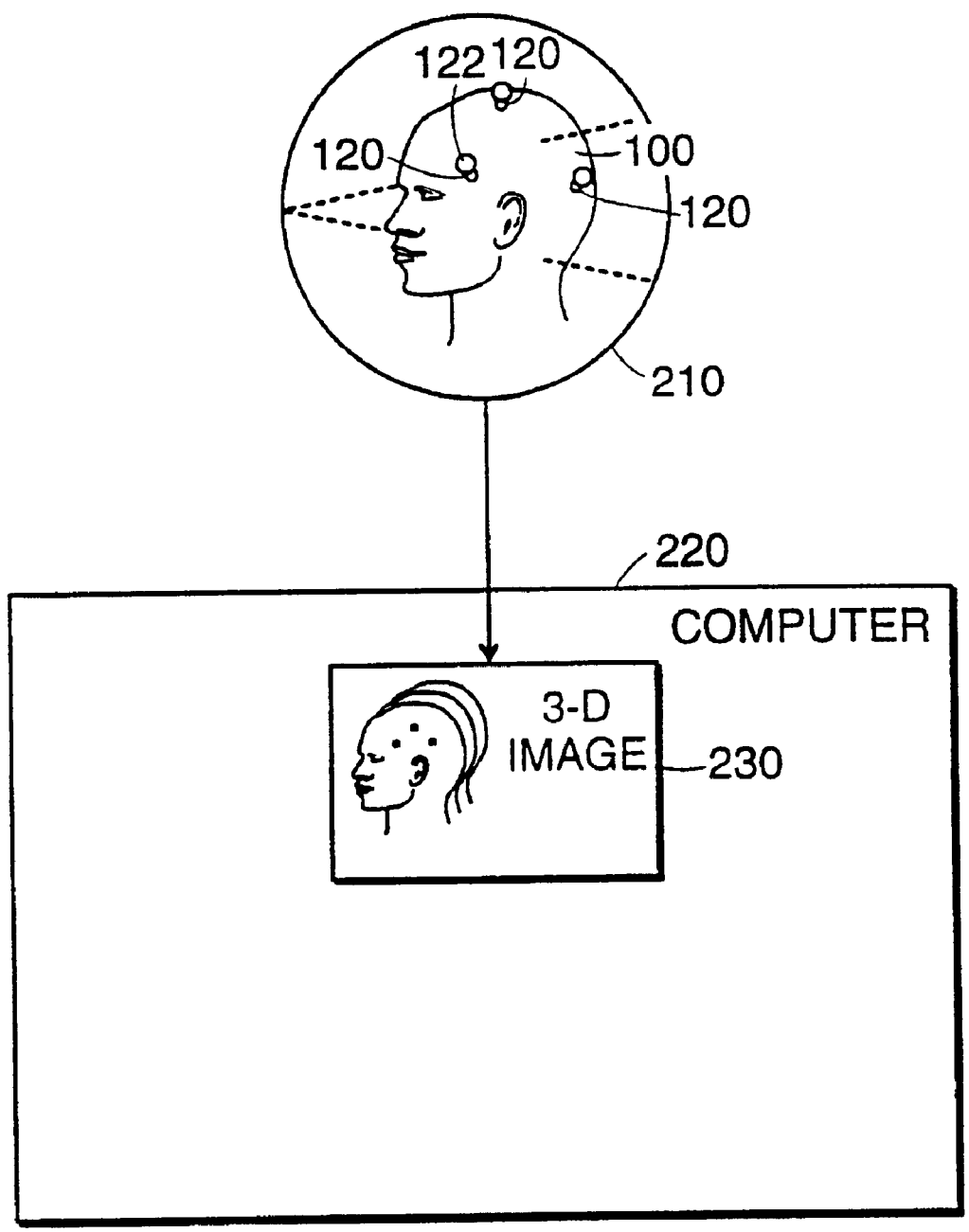
FIG. 2 illustrates a scanning phase.

Referring to FIG. 2, after scanning markers 122 are attached to bone anchors 120, the patient is scanned in a scanner 210 (illustrated schematically) producing a three-dimensional image 230. This image is transferred to a computer 220 where it is stored.

After the scanning process is complete, scanning markers 122 are removed from the patient, but bone anchors 120 are left firmly in place. In a typical situation, because the surgical phase of the process will not begin for several hours, or even several days, the patient is allowed to walk around or even allowed to return home at this point.

Figure 3:
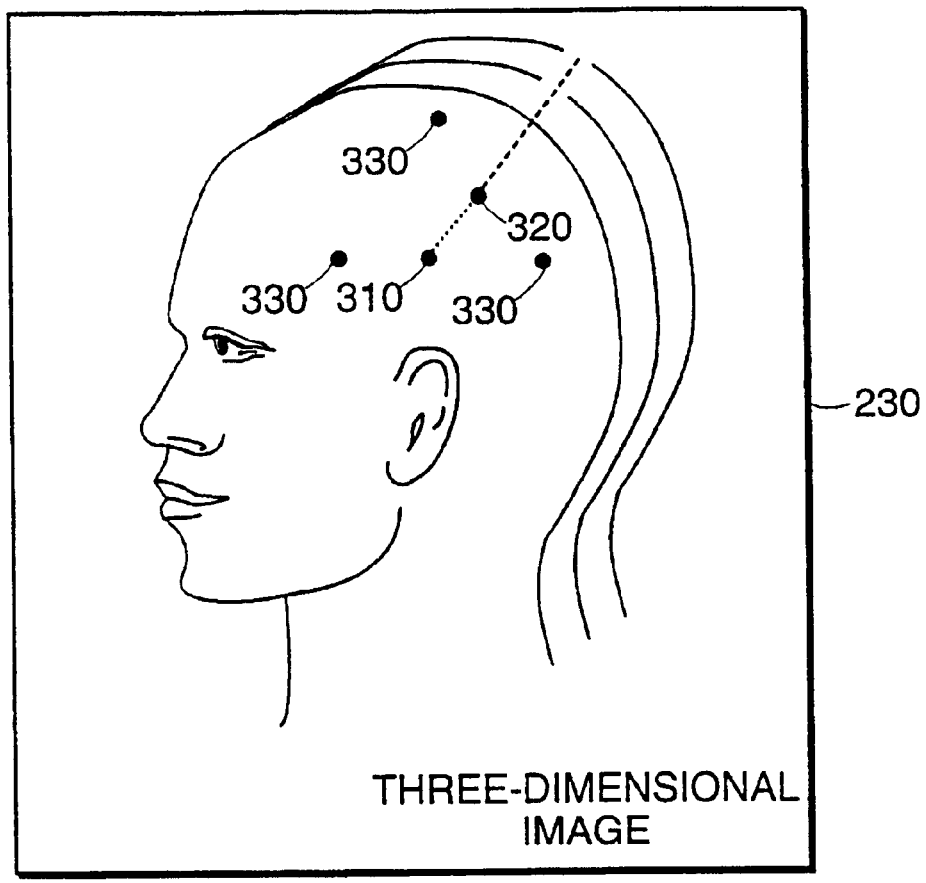
FIG. 3 illustrates a scanned image and located image points.

Referring to FIG. 3, a surgeon plans the upcoming surgery using a computer display of image 230 using well-known techniques in stereotactic surgery. The surgeon identifies a target image point 310 in image 230 corresponding to a target point in the body. The three dimensional coordinates of the target image point in the coordinate system of image 230 are stored on the computer. The surgeon also identifies an entry image point 320 defining a straight-line trajectory by which a surgical instrument can reach the target point while avoiding critical structures in the brain. The coordinates of the entry image point are also stored.

Referring still to FIG. 3, marker image points 330 in image 230 correspond to the marker portions 126 of scanning markers 122 (FIG. 1b). The surgeon can locate these points using the computer display in a similar manner to locating the target and entry points. Alternatively, an automated algorithm is implemented on computer 220 to locate marker image points 330 based on the image characteristics, such as brightness or shape, of the points. In either case, the coordinates in the image of marker image points 330 are stored.

At this point, based on a known correspondence of the scanned image to the physical body, the locations of the actual target and entry points on the body with respect to the locations of the scanning markers are computed and stored on the computer. This computation is based on the stored coordinates of the corresponding marker, target, and entry image points.

A representation of the surface of the skull can be computed directly from the scanned image using well-known image processing techniques. This surface representation can be used to ensure that a designed fixture will properly fit over the skull, or to determine other characteristics of the skull that may be used to design the fixture.

This completes the scanning and surgical planning stage.

Fixture Design Phase

Figure 4:
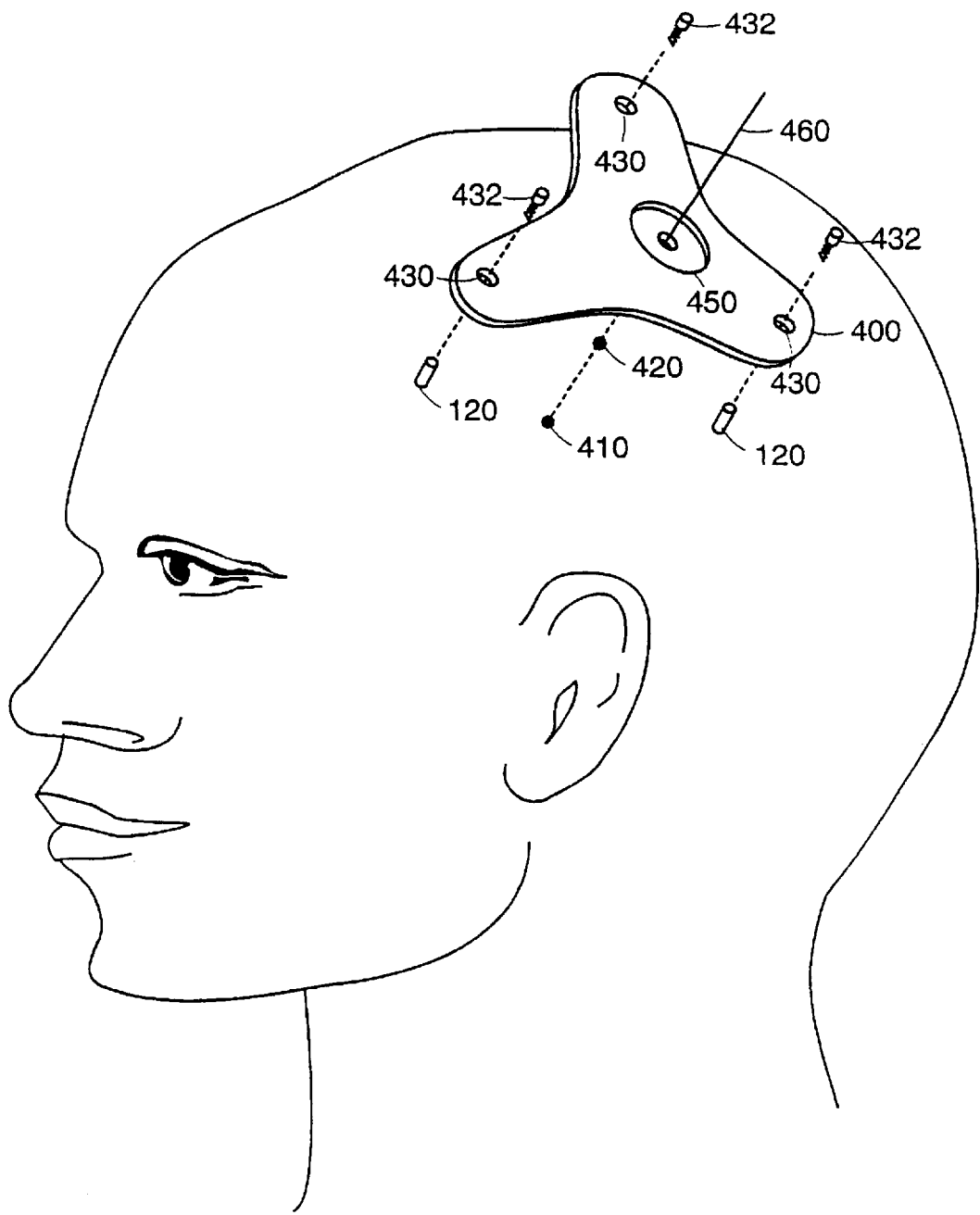
FIG. 4 illustrates a customized fixture.

The next phase of the process involves design and fabrication of the fixture itself. The design requirements of the fixture can be understood by referring to FIG. 4 which shows how a fabricated fixture 400 will be attached to bone anchors 120 in the surgical phase. In this embodiment, fixture 400 is attached to bone anchors 120 using bolts 432 which pass through openings 430 in fixture 400. When attached to the bone anchors, mounting points of fixture 400 are located at the prior locations of the marker portions 126 of scanning markers 122.

A planned actual trajectory 460 passes through an actual entry point 420 to an actual target point 410 corresponding to the planned entry image point 320 and target image point 310 (FIG. 3). Trajectory 460 passes through fixture 400 when attached to the skull.

Fixture 400 includes a way of mounting an instrument guide onto it to guide a surgical instrument along trajectory 460. In this embodiment, fixture 400 includes a mounting base 450 for attaching an instrument guide. Mounting base 450 has a flat surface with a central opening. When fixture 400 is attached to the skull, trajectory 460 passes through the central opening of the mounting base and the flat surface of mounting base 450 is perpendicular to trajectory 460. The distance between target point 410 and the mounting base is also determined before the surgical phase, for example by designing the fixture so that this distance is a standard distance related to the type of instrument that will be used.

The design of fixture 400 for a particular patient and surgical procedure must satisfy several constraints including one or more of the following:

mounting base 450 is centered on the planned trajectory and oriented perpendicular to the trajectory, the mounting points of fixture 400 mate with bone anchors 120, the distance between target point 410 and the mounting base must be an exact distance or within a particular range related to the surgical instrument and guide that will be used, the orientation of the fixture at each of the mounting points must be appropriate for the orientation of the corresponding bone anchors, and the fixture must provide sufficient clearance above the skull when mounted.

Figure 5A:
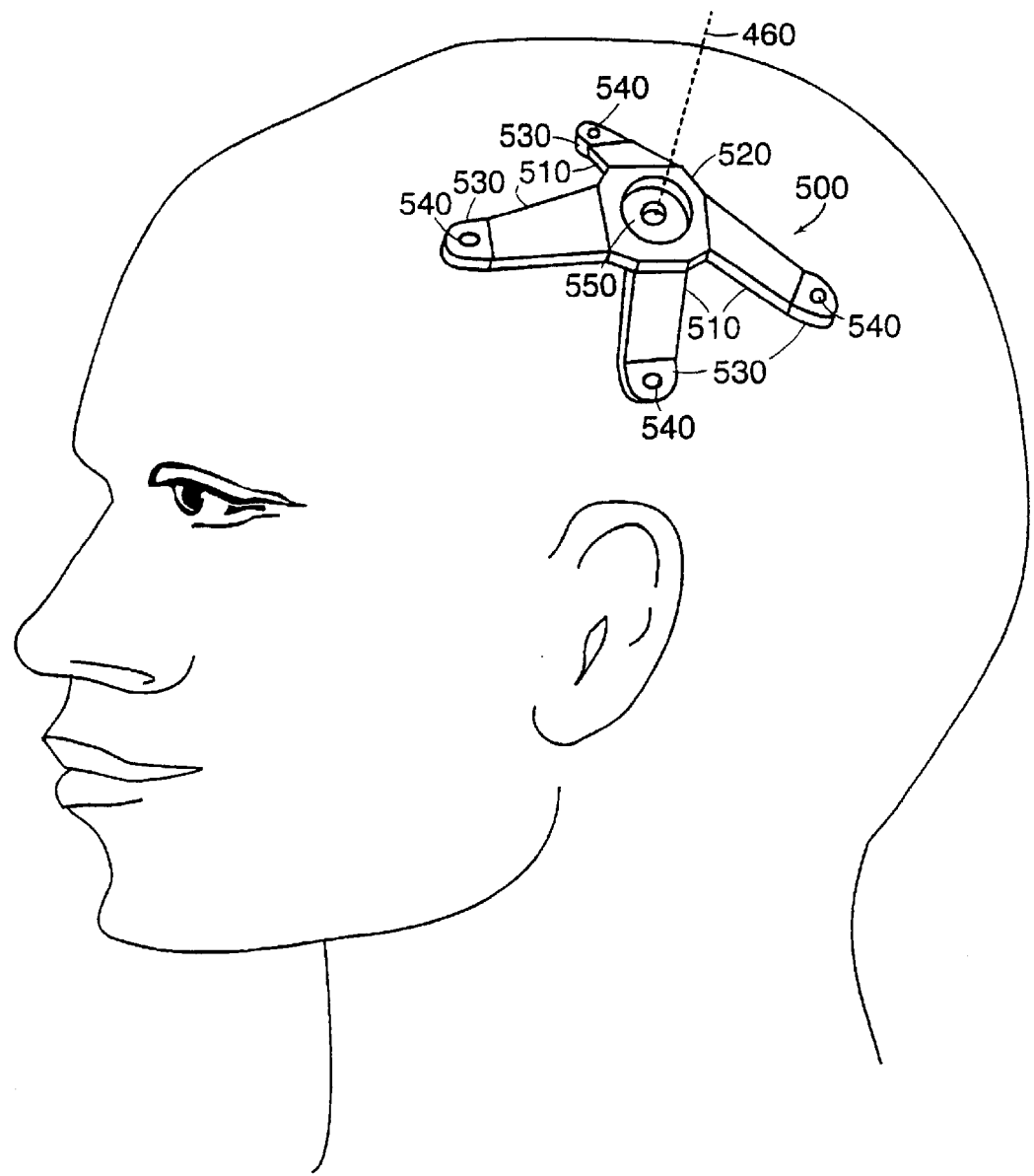
FIGS. 5a–c illustrate another customized fixture, attached to a head, and viewed along a target trajectory and from the side.
Figure 5B:
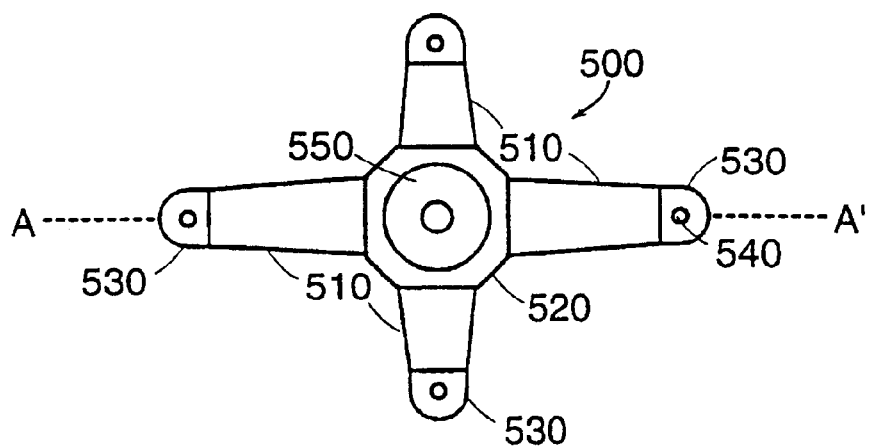
Figure 5C:
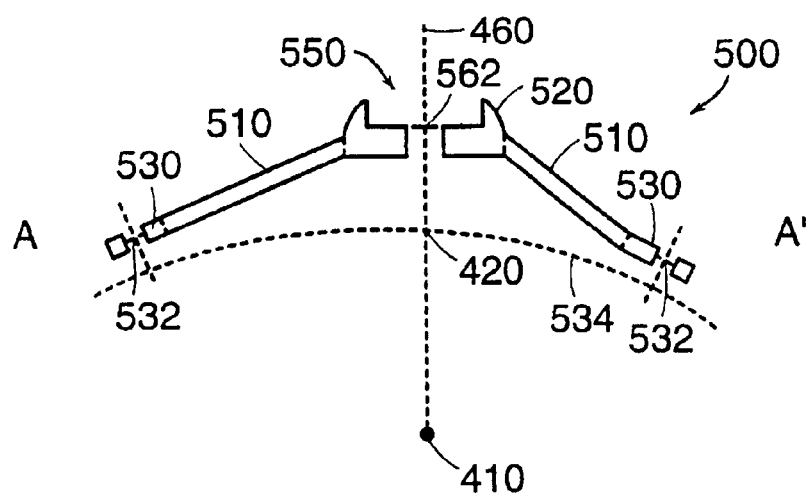

Referring to FIGS. 5a–c, an second exemplary fixture 500 is shown attached to the patient's head (FIG. 5a) and shown in a view along the planned trajectory (FIG. 5b) and in cross section (FIG. 5c). Fixture 500 is designed to attach to four bone anchors. Fixture 500 has a central mounting base 550 in a center section 520. Four "legs" 510 extend from the center section to four mounting pads 530 with mounting holes 540 through which fixture 500 is attached to the bone anchors.

The procedure for satisfying the constraints identified above uses an algorithmic approach. The approach can be understood with reference to FIGS. 5b–c. Referring to FIG. 5c, mounting base 550 is centered on planed trajectory 460. In this example, the distance between target point 410 and the center point 562 of the mounting base is set to a predetermined fixed distance.

Referring still to FIG. 5c, two of the mounting points 532 are illustrated along with the axes of the bone anchors. Mounting pads 530 are designed as planar sections to lie over the mounting points and to be perpendicular to the axes of the bone anchors. Legs 510 are then designed as planar sections that join mounting pads 530 and center section 520.

In FIG. 5c, the surface of the skull 534 is illustrated along with entry point 420. The mounting pads, legs, and center section are design to lie above and provide sufficient clearance above the skull.

In order to orient mounting pads 530 perpendicularly to the axes of the bone anchors, this approach to designing fixture 500 relies on knowledge of the orientations as well as the locations of the bone anchors. In the approach described above, as shown in FIG. 1b, a single marking portion 126 is attached in scanning marker 122 to each bone anchor 120. Therefore only the location of each bone anchor is determined by locating the marker images of the scanning markers.

One of several alternative approaches to determining the orientation of the bone anchors can be used. First, alternative scanning markers 122 can be used. The alternative scanning markers have two marking portions 126 separated along the axis of the scanning marker. Locating the images of both the marking portions determines the orientation of the bone anchor. A second alternative is to use a normal direction to a surface models of the skull. The surface model of the skull can be computed directly from the scanned image using well known image processing techniques. A third alternative is to approximate the orientation of the bone anchors by fitting a surface through the locations of the scanning markers, and optionally through the entry point. A fourth alternative is to not rely on the mounting pads being normal to the axes of the bone anchors, relying instead on a mounting approach that is less sensitive to the orientation or the anchors. For instance, a ball can be mounted on each bone anchor and the fixture can have corresponding sockets which mate with the balls.

Fixture 500 shown in FIGS. 5a–c is made up of essentially planar sections. Alternative algorithmic design approaches can be used to design curved structures. For instance, the shape of the fixture can be determined using a surface spline with the mounting points and the mounting base being points at which constraints on the coefficients of the splines are determined.

The design of the customized fixture is converted into a computerized specification of a solid model. A solid model is a computer representation of a volume enclosed by a surface surrounding the entire volume. Various types of computer representations of the volume can be used. A common format is an ".stl" file that is used by many computer aided design (CAD) systems. The stl file includes a set of representations of surface patches that together define a complete surface that encloses the volume. The stl file for the designed fixture is then used as the specification for fabrication of the fixture.

Fixture Fabrication

The solid model file is transferred to a rapid prototyping and tooling (RPT) machine. The file can be transferred on a physical medium, such as a magnetic disk, sent over a data network, or used directly on the computer on which is was computed.

A variety of RTP techniques can be used to fabricate the fixture. In this embodiment, a Fused Deposition Modeling (FDM) machine, such model FMD2000 manufactured by Stratasys, Inc. of Eden Prairie Minn., is used to make the three dimensional fixture from the .stl file. The FDM machine essentially robotically lays down a long ribbon of extruded material thereby slowly building up the modeled fixture. As material is laid down, it fuses with the previously laid down material making a homogeneous solid. The process results in a highly accurate fixture, within 5 mil of the specification in the .stl file. Various materials can be used for the fixture. In the embodiment, medical grade ABS is used.

After fabrication in the FDM machine, some further machining may be needed for some fixture designs. For instance, the ABS material can be drilled and tapped to provide mounting points at which an instrument guide is attached.

Surgery

The completed fixture is returned to the surgeon. The patient returns, with the bone anchors still intact, for the surgical phase. The fixture is sterilized and then the surgeon attaches the sterilized fixture to the bone anchors in the patient's skull and begins the surgical phase.

The surgical phase for brain surgery involves several steps, including opening a burr hole, and the inserting of an instrument in the burr hole. The burr hole can be drilled prior to attaching the fixture, or can be drilled using the fixture. In the latter case, a drill guide is attached to the mounting base and a drill is inserted through the drill guide to drill the burr hole at the planned entry point.

Figure 6:
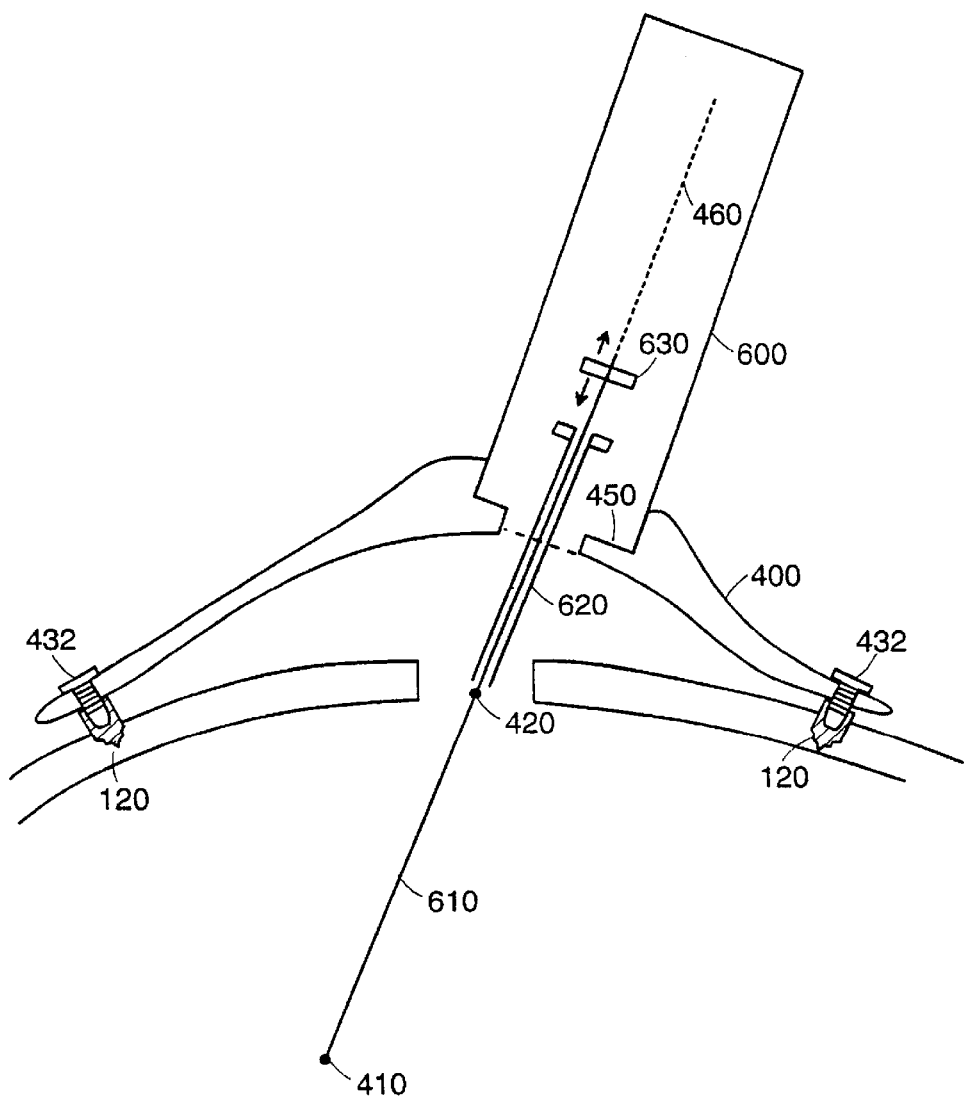
FIG. 6 is a side view of a fixture supporting an instrument guide.

Referring to FIG. 6, to insert a surgical instrument into the brain to reach the planned target point, fixture 400 is used to support an instrument guide 600. In the illustrative example shown in FIG. 6, instrument guide 600 supports an insertion tube 620 through which an instrument 610, such as a recording electrode, is passed. The instrument is attached to a drive 630 on instrument guide 600 for manually or automatically driving the instrument to target point 410. Since the separation of target point 410 and mounting base 450 is specified when the fixture is designed, if the length of the surgical instrument is predetermined, then the instrument guide can be calibrated to precisely insert the instrument to the target point. For instance, if the instrument is known to have a standard length, the separation of the target point and the mounting base on the fixture can be designed such that when the instrument drive is in its fully inserted position, the instrument has reached the planned target point.

Figure 7:
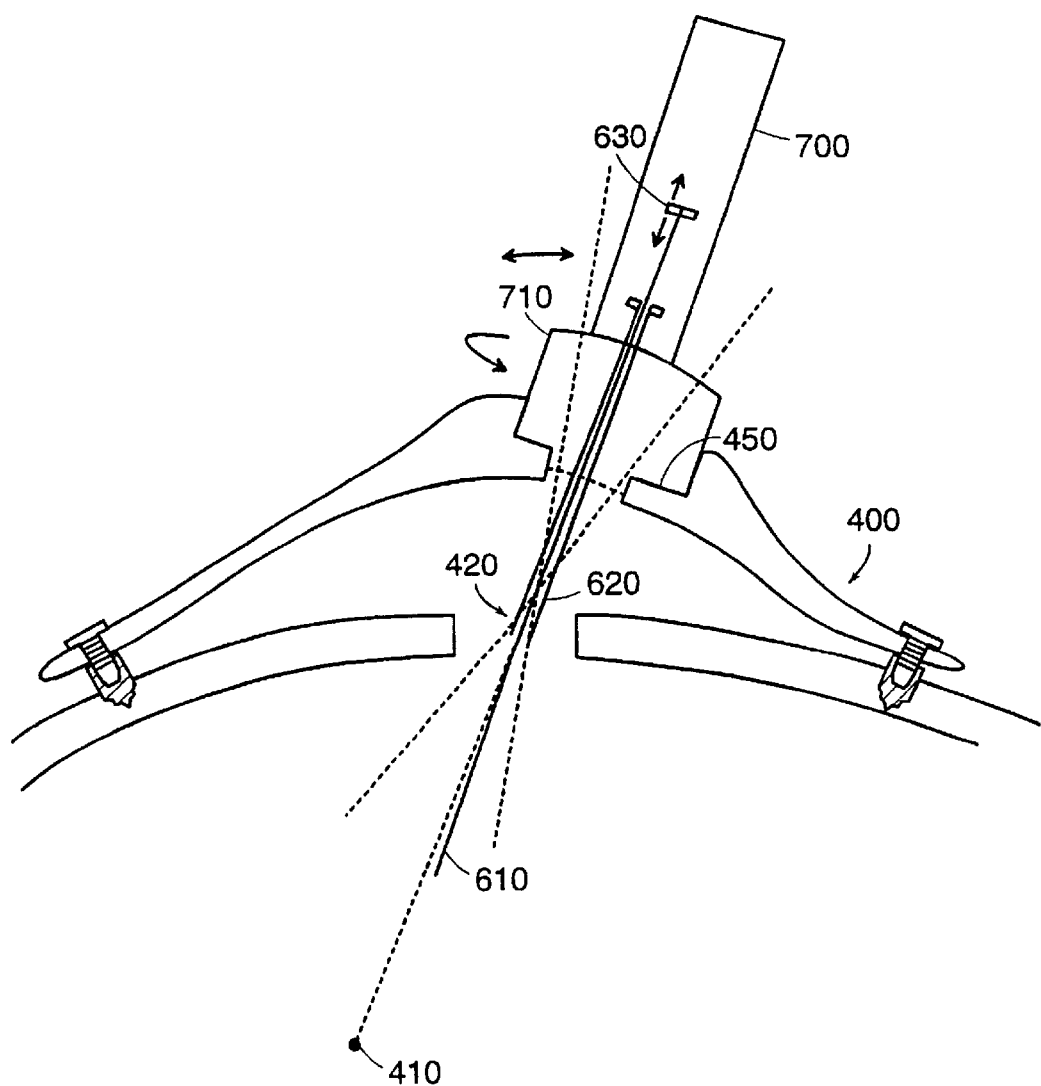
FIG. 7 is a side view of a fixture supporting an adjustable instrument guide.

Alternative instrument guides can be used in conjunction with a custom fabricated fixture. Referring to FIG. 7, an adjustable instrument guide 700 is attached to mounting base 450. The instrument guide is adjustable allowing the actual trajectory of instrument 610 to fall within a cone with an apex at entry point 420. For instance, an adjustable guidance fixture such as one described in copending U.S. patent application Ser. No. 09/063,658 filed Apr. 21, 1998 or Provisional Application 60/096,384 filed Aug. 12, 1998 can be used. Both of these copending applications are incorporated herein by reference.

Note that since adjustable instrument guide 700 is attached in a precise relationship to target point 410 and entry point 420, a "registration" step of the type typically carried out in stereotactic surgery, used to conformally map a physical coordinate system to an image coordinate system, is not needed. Furthermore, instrument guide 700 can include encoders that generate signals which encode the adjustment of the actual trajectory relative to the planned trajectory, allowing precise visual feedback to be computed and displayed to a surgeon. Instrument guide can also be actuated allowing remote or robotic control of the instrument and the guide.

Alternative Approaches

Figure 8:
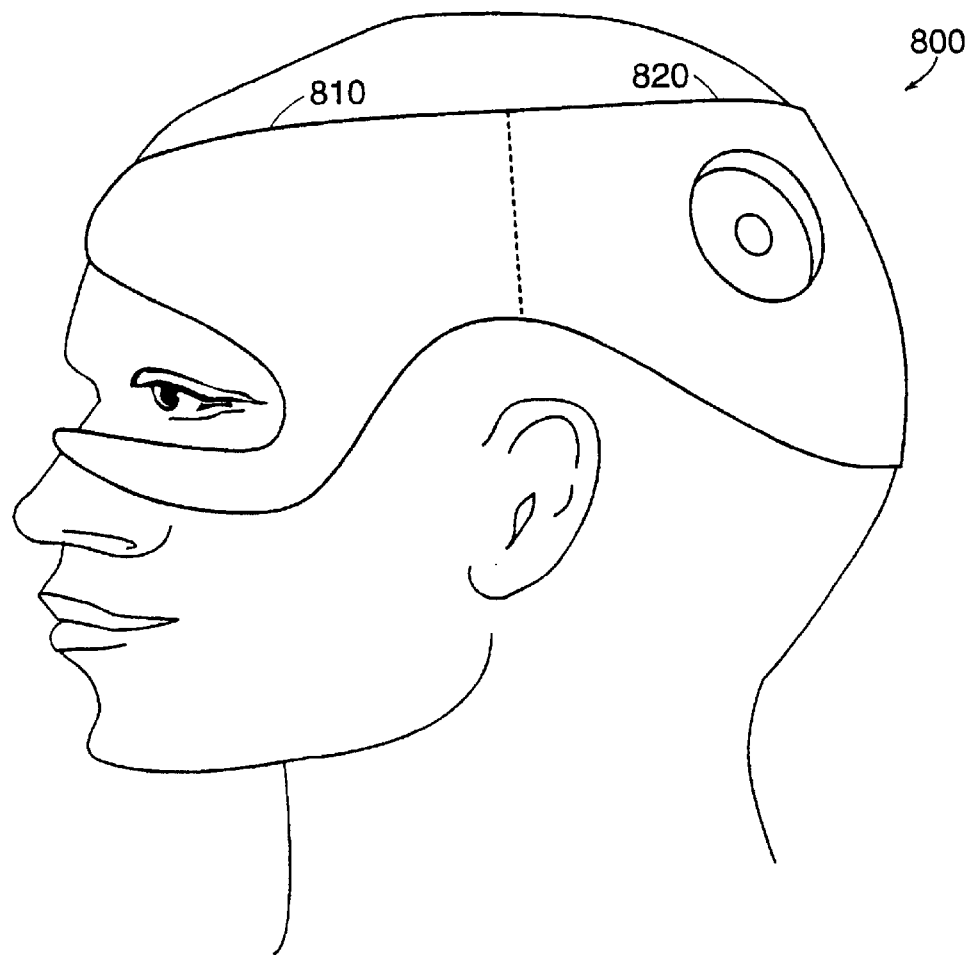
FIG. 8 illustrates a head-mounted fixture which mates with the contours of the skull.

In the embodiment described above, the fabricated fixture is attached to bone anchors. Alternative embodiments attach the fixture to the body in different ways. For instance, other types of inserts or bone anchors can be attached to the skull. Also, rather than attaching the fixture to a bone anchor, the fixture can be designed to precisely clamp onto the patient's head. For example, referring to FIG. 8, two mating halves 810, 820 of a fixture 800 match the contours of cheek bones and forehead, and the contours of the back of the head, respectively. The contours of the patients head are derived from the a model of the skull that is computed automatically from the scanned image.

In the embodiments described above, the design (i.e., the solid model) of the fixture is determined algorithmically from the locations and orientations of points, including the mounting points, the target point and the entry point. An alternative approach to design of the fixture involves interaction with the surgeon. Rather than having to specify a detailed design for the fixture, the surgeon has control over a limited number of deformations of a standard fixture.

A particular implementation of this deformation procedure uses a relational geometry approach. U.S. Pat. No. 5,627,969 issued Mar. 17, 1995 to John S. Letcher, Jr., describes such a relational geometry approach and software architecture to implement the approach.

A set of "standard" fixtures are used as the basis of the procedure. Each of the standard fixtures is described using a "logical model" in which geometric relationships of various elements of the fixture are explicitly identified. Examples of constraints described in the logical model include the shape of the mounting base (which is not deformed), and the connections of sections such as the mounting legs and central section.

In the fixture design phase, the surgeon selects one of the standard fixtures. Using a computer aided graphic design (CAGD) tool, the surgeon views both a representation of the body and a representation of the fixture. Initially, the standard fixture does not satisfy any of the design constraints. Using the CAGD tool, the surgeon adjusts the fixture design so that the fixture will mate with the bone anchor, and so that the mounting base will have the correct location and orientation with respect to the entry and target points. Furthermore, the surgeon can adjust other aspects of the design, for example, deforming the fixture to allow sufficient clearance for an ear.

Spinal Surgery

Another embodiment of the invention is directed to spinal surgery. As in the brain surgery approach, a three-dimensional scanned image is taken of the patient, in this case of his or her spine. In this embodiment, no anchor points or scanning markers are necessarily applied to the spine, however.

Figure 9A:
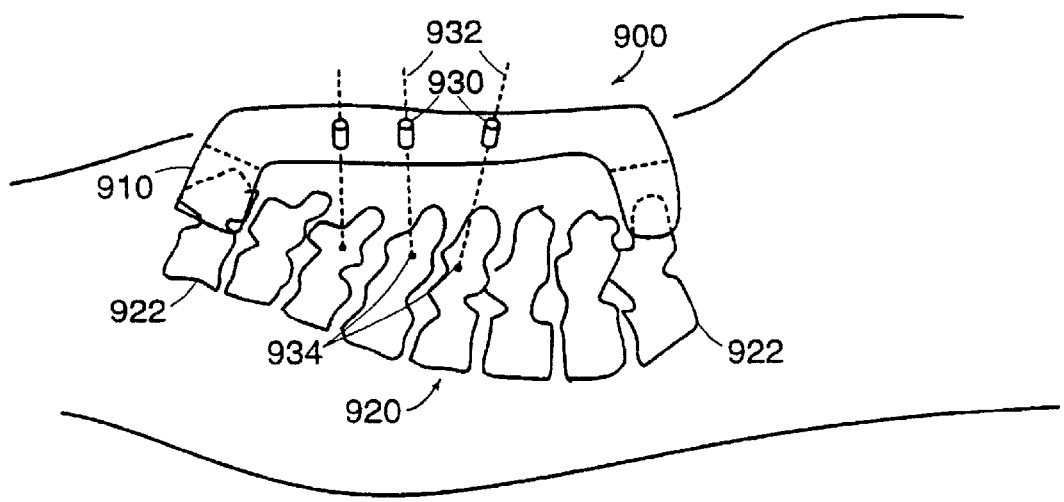
FIGS. 9a–b illustrate a customized fixture for spinal surgery.

Referring to FIG. 9a, using techniques well known in stereotactic spinal surgery, the surgeon identifies target points 934 in the image of a spine 920, for example, points at which screws are to be inserted into the spine. The surgeon also plans trajectories 932 to reach the target points, for example determining the angles at which the screw holes will be drilled.

Using well-known image analysis and modeling techniques, a computer model of the segments of the spine 920 is formed from the scanned image.

Figure 9B:
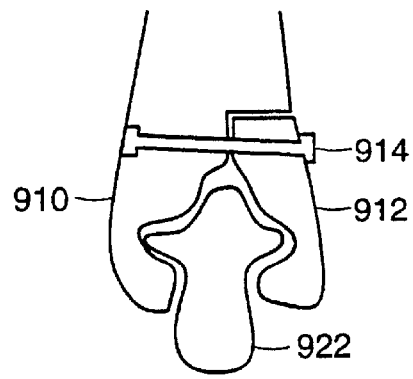

The surgeon identifies two segments 922 to which a customized fixture 900 is to be attached. Referring to FIG. 9b, the models of segments 922 are used to form clamp sections which mate with the contours of the segments. A portion 910 of the clamp section is formed in one piece with the main section of the fixture. A second portion 912 of each clamp section is formed as a separate component. The two portions of the clamp section are drawn together to attach the fixture to the spinal segments. Fixture 900 is formed to match the curvature of spine 920 as it is scanned. For instance, the separation of segments 922 matches the separation in the scanned image.

For each of the target points, a separate instrument guide 930 is formed in fixture 900. For example, each instrument guide can be a elongated hole into which a drill is inserted. The instrument guides can be designed so that not only the orientation but also the depth of the holes drilled into the spinal segments are precisely determined by the instrument guides.

After attaching the fixture, the surgeon proceeds with the operations on each of the spinal segments that are involved in the overall surgery without repositioning fixture 900.

In an alternative embodiment directed to spinal surgery, previously applied anchors and scanning markers in spinal segments or bony structures are used to define the geometry of a customized fixture so that it mates with these anchors.

Another embodiment directed to spinal surgery not only addresses operations to be performed on the spine in the configuration that it was scanned, but also address manipulating the spine to a desired curvature different from that in the scanned image. In addition to forming a computer model of the spine as it is scanned, a modified spinal model is also derived. The modified model represents the desired curvature of the spine. A second fixture is designed according to the modified model. After the first fixture is removed, the second fixture is attached to achieve the desired curvature of the spine.

Figure 10A:
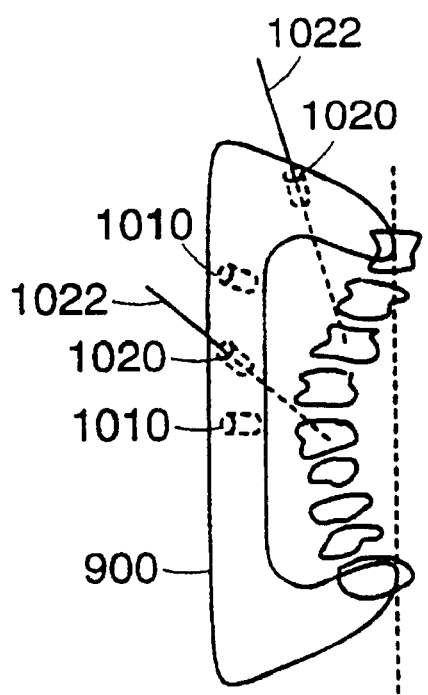
FIGS. 10a–b illustrate a spinal fixture used to modify the curvature of the spine.
Figure 10B:
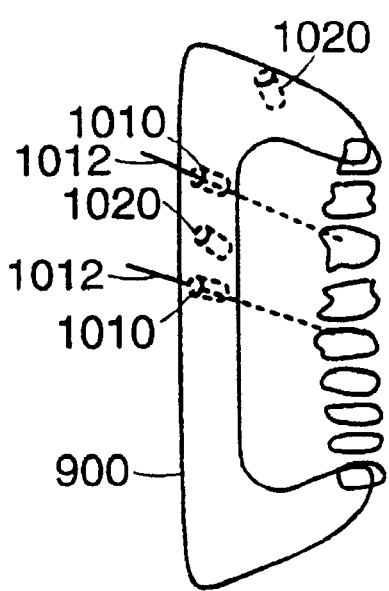

A related embodiment is illustrated schematically in FIG. 10a–b. This embodiment also uses the modified spinal model. However, rather than forming a second fixture, additional guides 1010 are formed in the first fixture for the purpose of manipulating the spine into the desired configuration. For example, in addition to guides 1020 which are formed along the orientations 1022 to drill the segments, additional guides 1010 are formed in the fixture corresponding to the orientations 1012 of the drilled holes after modification of the curvature, and screws inserted into the holes can be forced to lie in the desired orientations. Similar embodiments can be applied to correction and repair of orthopedic bone or joint deformity or fracture.

Other Surgical Procedures

The embodiments presented above are described in the context of stereotactic brain or spine surgery. Similar approaches are applicable to other types of stereotactic surgery.

Similar customized fixtures are also applicable to other types of surgical procedures in which a device must be precisely attached to a body. For instance, a precise instrument guide can be mounted with reference to facial features for eye surgery.

Sensor-Tracked Image Guidance

Figure 12:
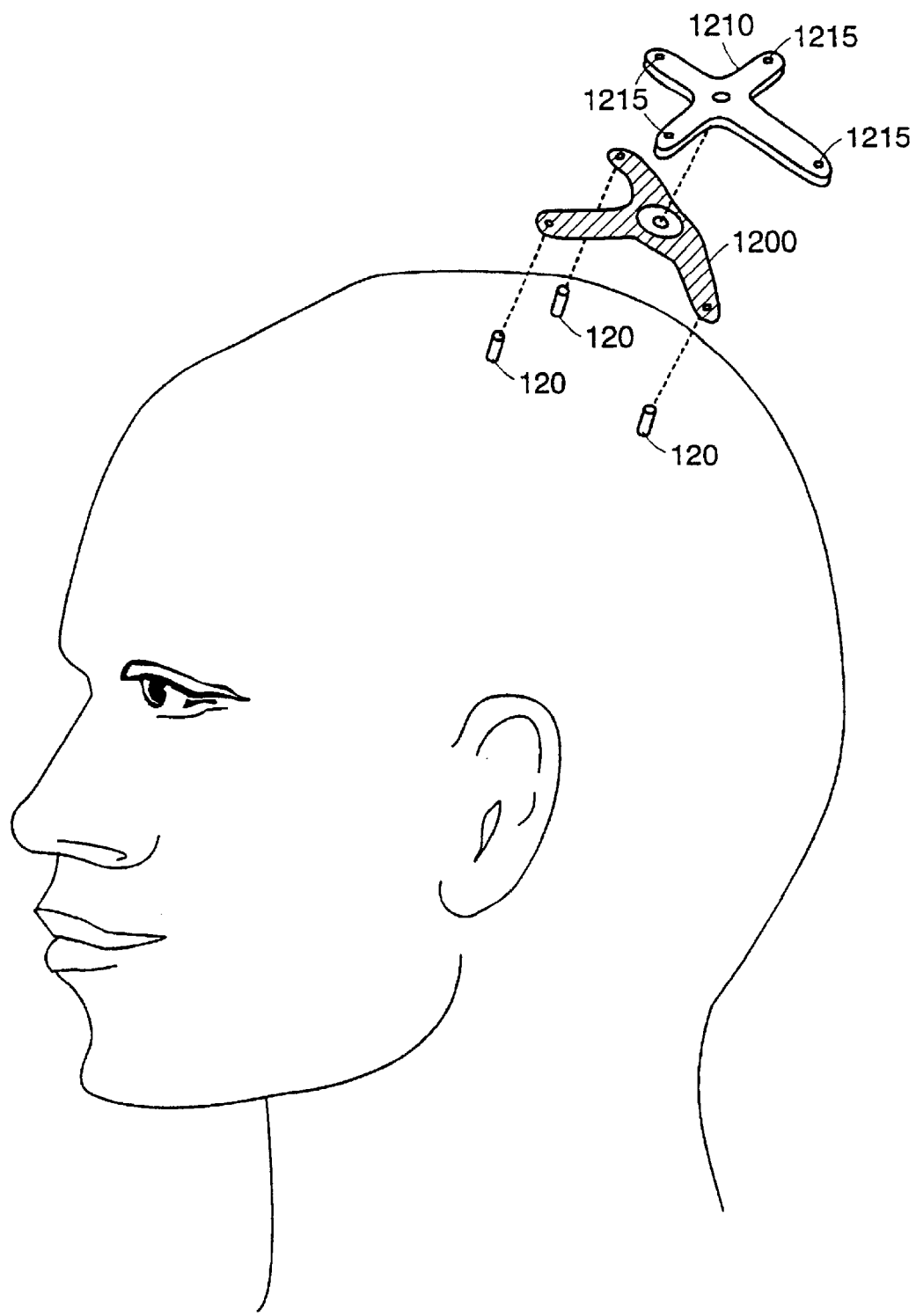
FIG. 12 illustrates attachment of tracking markers to a customized fixture.

In other alternative embodiments, one or more customized fixtures are used to support tracking markers that are used in sensor-tracked image-guided stereotactic surgery. Referring to FIG. 12, in an exemplary embodiment in which tracking markers are used, bone anchors 120 are attached to a body. In a procedure of the type described above, scanning markers are attached to the bone anchors, and the precise location of the bone anchors relative to the body are determined from a scanned image.

Referring still to FIG. 12, a customized fixture 1200 is fabricated so that it has a known geometry relative to the mounting points which mate with bone anchors 120. In this embodiment, a tracking fixture 1210 is attached to customized fixture 1200. Tracking fixture 1210 has a number of tracking markers 1215 attached to it. These markers are tracked during surgery. Tracking markers 1215 light-emitting diodes, or other emitters or reflectors of energy, whose three-dimensional location can be tracked using a remote sensing device, such as a camera array or a laser tracker.

Figure 13:
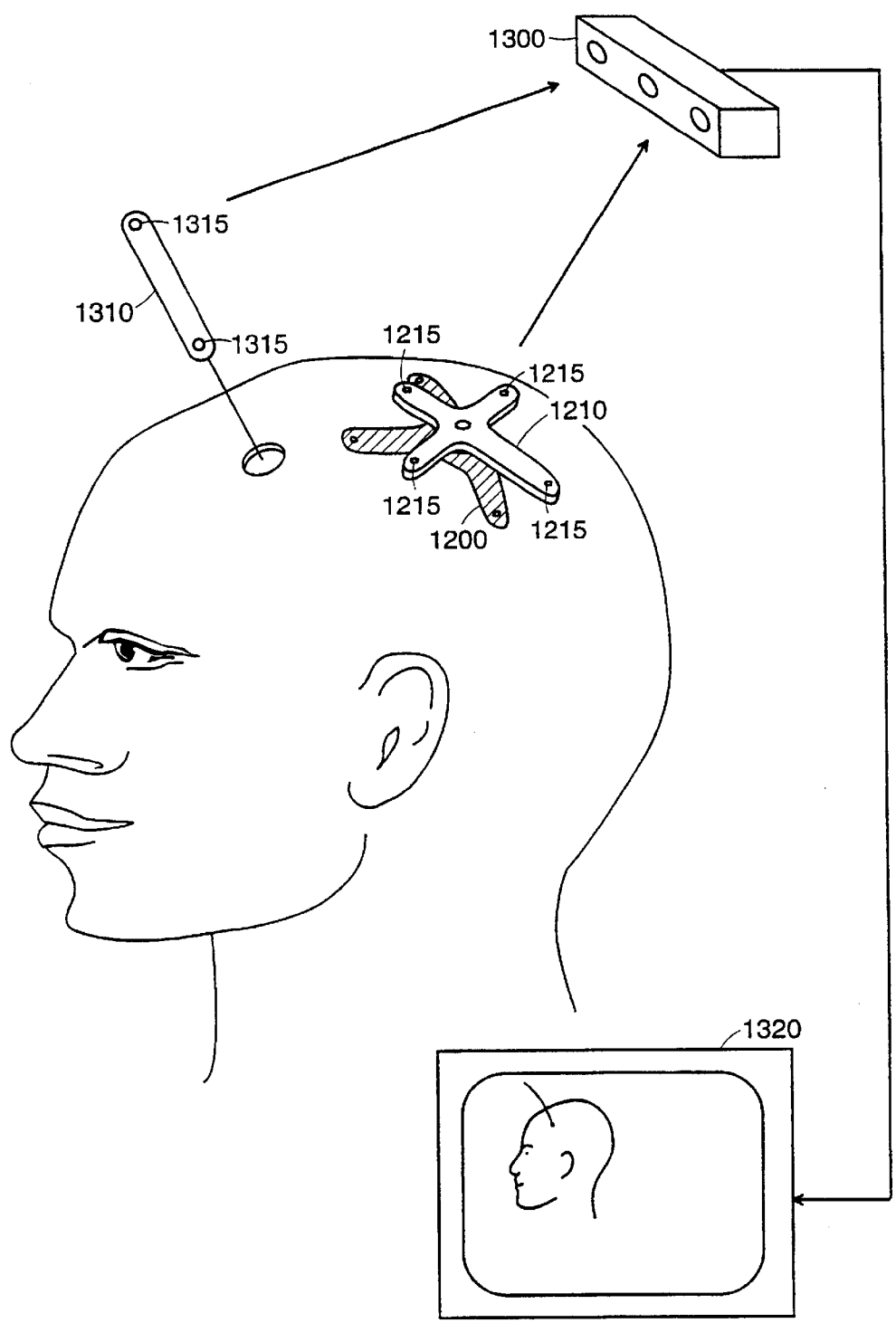
FIG. 13 illustrates sensor-tracked image guidance of a surgical instrument relative to tracking markers attached to a skull with a customized fixture.

Referring to FIG. 13, tracking fixture 1210 is shown rigidly mounted to the body through bone anchors 120. The locations of bone anchors relative to the body is determined from the scanned image. The geometry of customized fixture 1200 is determined in the fixture design phase. The location of tracking markers 1215 on tracking fixture 1210 are known from the predetermined geometry of the tracking fixture. The locations of tracking markers 1215 relative to bone anchors 120 are then computed from the geometry of the customized fixture and the geometry of the tracking fixture attached to it, in what is essentially a "computed registration" step.

Referring still to FIG. 13, a surgical instrument 1310, for example a manually positioned probe, also includes multiple tracking markers 1315. A tracking system, which includes a remote sensing device 1300, in this case a camera array, is used to track the three-dimensional locations of tracking markers 1215 and 1315. Using a predetermined geometry of surgical instrument 1310, including the locations of tracking markers 1315 on the instrument, and the determined locations of tracking markers 1215 relative to the bone anchors. The tracking system is used to compute the relative position of the surgical instrument to the body. The tracking system displays a representation of surgical instrument 1310 on display system 1320 in a proper position and orientation relative to an image of the body.

Note that a manual registration phase of the type generally performed prior to conventional image-guided stereotactic surgery is not needed to determine the relative position of the instrument to the body. However, the computed registration step described above can be validated or double-checked using a manual procedure, for example, by touching the end of the surgical instrument to predetermined locations, such as the locations of the bone anchors, and verifying that the tracking system correctly calculates the locations. Furthermore, remote sensing device 1300 does not have to remain in a fixed location relative to the body, and in fact, both the body and sensing device 1300 can be freely moved around while continually tracking the location of the surgical instrument relative to the body.

Figure 14:
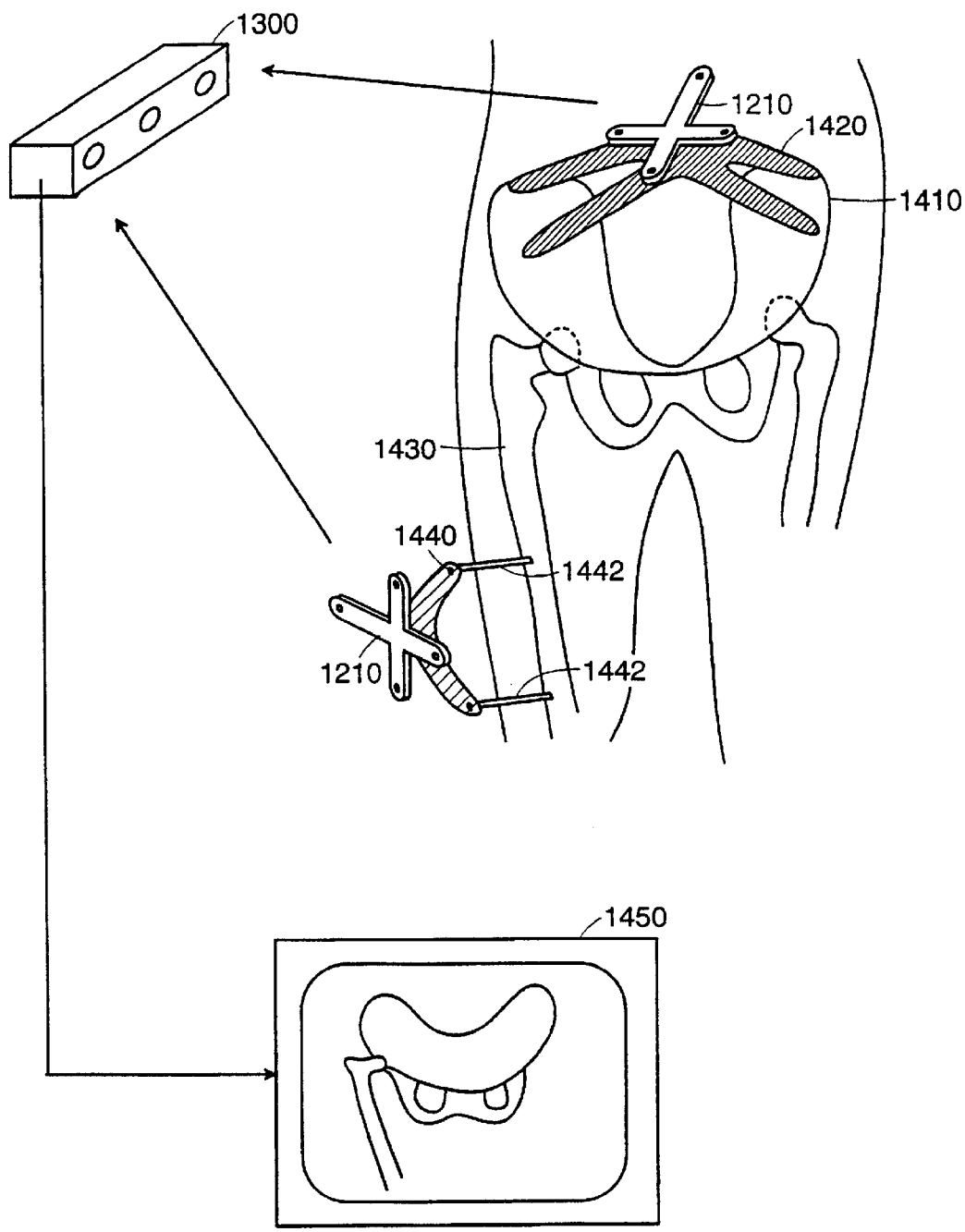
FIG. 14 illustrates multiple customized fixtures supporting tracking markers used to track the position of a femur relative to a pelvis.

Referring to FIG. 14, in another alternative embodiment, multiple tracking fixtures 1210 are used. Tracking fixtures 1210 are rigidly attached to segments of an articulated portion of the body to track the relative positions of those segments. In one exemplary use of multiple tracking fixtures, as shown in FIG. 14, one tracking fixture 1210 is attached to a pelvis 1410 using a first customized fixture 1420, while a second tracking fixture 1210 is attached to a femur 1430 using a second customized fixture 1440. Customized fixtures 1420 and 1440 are designed and fabricated in the manner described above to mate with mounting anchors or screws on the pelvis and femur. For instance, anchoring screws 1442 are inserted into femur 1430. Scanning markers are attached to anchoring screws 1442 prior to scanning. Customized fixture 1440 is designed to have a known geometry and to mate with anchoring screws 1442. Customized fixture 1420 is similarly designed to mate with bone anchors that have been inserted into the pelvis.

During surgery, remote sensing device 1300 is used to determined the relative position and orientation of the two tracking fixtures 1210. Based on the computed registration of each tracking fixture to the rigid part of the body to which it is attached, the tracking system computes the relative position and orientation of femur 1430 and pelvis 1410 and displays representations of the femur and the pelvis on a display system 1450 in their proper geometric relationship.

Similar customized fixtures are used to attach tracking fixtures to other parts of the body, for example to mulitple segments of the spine. Multiple tracking fixtures can also be used to track the configuration of skeletal joints during surgery or during other medical procedures.

In embodiments described above, tracking fixtures, which have integrated tracking markers, are attached to customized fixtures. Alternatively, a customized fixture can be designed and fabricated to directly hold the tracking markers, thereby being a customized tracking fixture (or "tracking frame"), which has a predetermined geometric relationship between the mounting points of the fixture and the locations of the tracking markers.

Implementation

Figure 11:
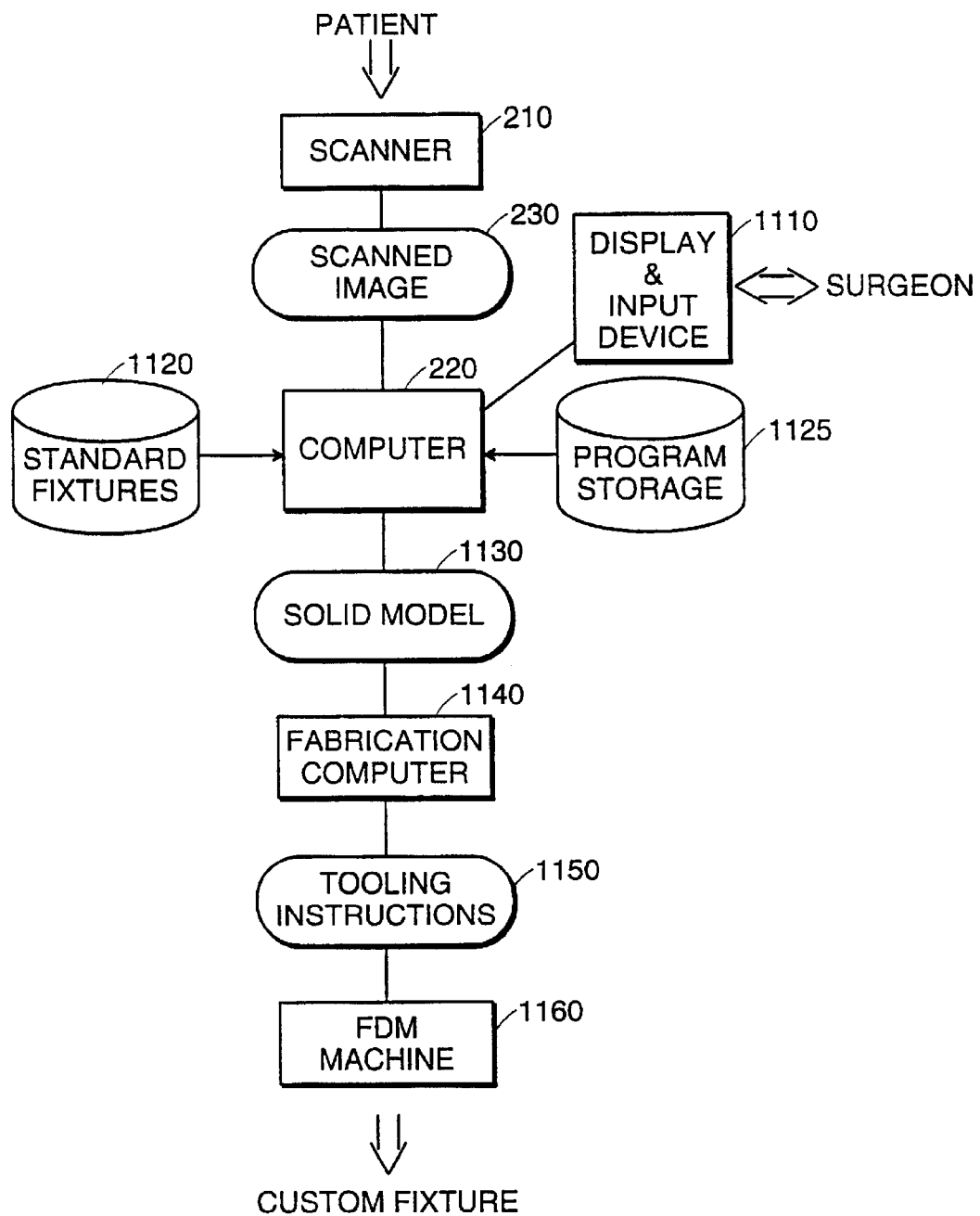
FIG. 11 illustrates a computer implementation of the fixture design procedure.

Referring to FIG. 11, the design and fabrication of the fixture involves several steps and pieces of equipment. Scanner 210 produces scanned image 230 which is passed to computer 220. Computer 220 is used by the surgeon to identify target and entry points, and possibly other points such as marker image points. A display and input device 1110 provides an interface for the surgeon. For instance, multiple planar views of the scanned image are presented to the surgeon, and the surgeon selects points using a mouse. Program storage 1125 is coupled to computer 220 for holding software used to implement procedures executed by computer 220. As described above, a library of standard fixtures 1120 can optionally be attached to computer 220. These standard fixtures are deformed using interactive procedures implemented on computer 220.

The product of the procedures executed on computer 220 is solid model 1130 which completely specifies the shape of the fixture. This model is passed to a fabrication computer 1140 which derives tooling instructions 1150 which are passed to the RPT machine 1160. The RPT machine fabricates the fixture according to the tooling instructions.

It is to be understood that the foregoing description is intended to illustrate and not limit the scope of the invention, which is defined by the scope of the appended claims. Other embodiments are within the scope of the following claims.

What is claimed is:

1. A method for forming and using a customized fixture comprising:

determining data characterizing a plurality of attachment locations on a body;

computing a digital model of the shape of the customized fixture, including determining said shape to mate with the attachment locations on the body and determining a location for attaching a tracking device to the fixture; and computing registration data that is sufficient to relate coordinates of a point in an internal coordinate system that is fixed relative to the attachment locations on the body with coordinates of said point in an external coordinate system in which a position of the tracking device that is attached to the body using the customized fixture is known.

2. The method of claim 1 further comprising using the registration data to relate coordinates of a point in the internal coordinate system and coordinates of said point in the external coordinate system.

3. The method of claim 2 wherein using the registration data includes transforming the coordinates of the point in the internal coordinate system to coordinates of said point in the external coordinate system.

4. The method of claim 2 wherein using the registration data includes transforming the coordinates of the point in the external coordinate system to coordinates of said point in the internal coordinate system.

5. The method of claim 4 further comprising using the coordinates of the point in the internal coordinate system to display a representation of the point in conjunction with a graphical image of the body.

6. The method of claim 4 wherein the point in the external coordinate system corresponds to a point that is fixed relative to an instrument that is free to move relative to the body.

7. The method of claim 6 further comprising tracking a position of the tracking device and a position of the instrument in the external coordinate system.

8. The method of claim 1 further comprising determining data characterizing the physical structure of the body by processing a three-dimensional scan of the body.

9. The method of claim 2 wherein determining data characterizing the attachment locations on the body includes identifying the attachment locations using the data characterizing the physical structure of the body.

10. The method of claim 9 wherein determining data characterizing the attachment locations includes determining positions of a plurality of bone anchors that were attached to the body at the time the three-dimensional scan was generated.

11. The method of claim 9 wherein determining data characterizing the attachment locations includes identifying a contour of a surface of the body for mating with the customized fixture.

12. The method of claim 1 further comprising providing the customized fixture.

13. The method of claim 12 wherein providing the customized fixture includes fabricating the customized fixture according to the digital model.

14. The method of claim 12 wherein fabricating the customized fixture includes forming a unitary structure of the fixture using a computer-controlled process.

15. The method of claim 14 wherein forming the unitary structure includes using a rapid prototyping and tooling (RPT) technique.

16. The method of claim 12 further comprising attaching the tracking device to the customized fixture at the determined location for attaching the tracking device.

17. The method of claim 16 wherein attaching the tracking device includes attaching a tracking frame that includes a plurality of tracking markers.

18. The method of claim 16 wherein the tracking device includes a plurality of tracking markers and attaching the tracking device includes attaching each of the tracking markers directly to the customized fixture.

19. The method of claim 16 further comprising attaching the customized fixture to the body by mating the mounting points with the mounting locations.

20. The method of claim 19 wherein the mounting locations include bone anchors attached to the body and attaching the customized fixture includes attaching the fixture to the bone anchors.

21. The method of claim 19 further comprising tracking a position of the tracking device in the external coordinate system.

22. The method of claim 21 wherein the tracking device includes a plurality of tracking markers and tracking the position of the tracking device includes tracking each of the markers relative to a sensing device.

23. The method of claim 22 wherein the external coordinate system is fixed relative to the sensing device and tracking each of the markers includes determining coordinates of the markers in the external coordinate system.

24. Software stored on a computer readable medium for causing a computing system to perform functions comprising:

determining data characterizing a plurality of attachment locations on a body;

computing a digital model of the shape of a customized fixture, including determining said shape to mate with the attachment locations on the body and determining a location for attaching a tracking device to the fixture; and computing registration data that is sufficient to relate coordinates of a point in an internal coordinate system that is fixed relative to the attachment locations on the body with coordinates of said point in an external coordinate system in which a position of the tracking device that is attached to the body using the customized fixture is known.

25. The software of claim 24 wherein the functions further comprise using the registration data to relate coordinates of a point in the internal coordinate system and coordinates of said point in the external coordinate system.

* * * * *

UNITED STATES PATENT AND TRADEMARK OFFICE
CERTIFICATE OF CORRECTION

PATENT NO.    : 6,738,657 B1
DATED         : May 18, 2004
INVENTOR(S)   : Joel I. Franck, Frederick C. Haer and Ronald J. Franklin It is certified that error appears in the above-identified patent and that said Letters Patent is hereby corrected as shown below:

Title page,
Item [63], Foreign Application Priority Data, delete "Continuation" and insert -- Continuation-in Part --;

Column 1,
Line 3, delete "continuation" and insert -- Continuation-in Part --;

Column 2,
Line 21, delete "a" after "such", insert -- as --;

Column 3,
Line 60, delete "attached", insert -- attach --;

Column 5,
Lines 5-10, delete and insert on line 4 after "126";

Column 6,
Line 38, delete "an", insert -- a -- before "second";
Line 62, delete "design", insert -- designed --;

Column 7,
Line 13, delete "models", insert -- model --;
Lines 36 and 38, insert a period before "stl";
Line 45, delete "is" after "which", insert -- it --; and Column 9,
Line 63, delete "a", insert -- an -- before "elongated".

Signed and Sealed this

Nineteenth Day of April, 2005

JON W. DUDAS
*Director of the United States Patent and Trademark Office*